US007723115B2

(12) United States Patent
Qian et al.

(10) Patent No.: US 7,723,115 B2
(45) Date of Patent: May 25, 2010

(54) MEASUREMENT OF DISTRIBUTED TOTAL ACID NUMBERS BY ELECTROSPRAY MASS SPECTROMETRY

(75) Inventors: Kuangnan Qian, Belle Mead, NJ (US); Kathleen E. Edwards, Freehold, NJ (US); Gary J. Dechert, Asbury, NJ (US); Stephen B. Jaffe, Moorestown, NJ (US); Larry A. Green, Mickleton, NJ (US); William N. Olmstead, Basking Ridge, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 951 days.

(21) Appl. No.: 11/499,788

(22) Filed: Aug. 4, 2006

(65) Prior Publication Data

US 2007/0037288 A1 Feb. 15, 2007

Related U.S. Application Data

(60) Provisional application No. 60/707,706, filed on Aug. 12, 2005.

(51) Int. Cl.
*G01N 31/00* (2006.01)
(52) U.S. Cl. .................................. 436/60; 436/173
(58) Field of Classification Search .................. None
See application file for complete search history.

(56) References Cited

OTHER PUBLICATIONS

Clemente et al. "A review of the occurrence, analyses, toxicity, and biodegradation of naphthenic acids", Chemosphere 60 (2005) 585-600.*
Qian et al. "Measurement of Total Acid Number (TAN) and TAN Boiling Point Distribution in Petroleum Products by Electrospray Ionization Mass Spectrometry", Anal. Chem. 2008, v. 80, pp. 849-855.*
PCT International Search Report.
Lo et al., "Electropray-Mass Spectrometric Analysis of Reference Carboxylic Acids and Athabasca Oil Sand Naphthenic Acids", Anal. Chem., 2003, v. 75, No. 23, pp. 6394-6400.
Qian et al., "Fundamentals and Applications of Electrospray Ionization Mass Spectrometry for Petroleum Characterization", Energy & Fuels, 2004, v. 18, pp. 1784-1791.
Qian et al., "Resolution and Identification of Elemental Compositions for More than 3000 Crude Acids in Heavy Petroleum by . . . ", Energy & Fuels, 2001, v. 15, pp. 1505-1511.

* cited by examiner

*Primary Examiner*—Yelena G Gakh

(57) ABSTRACT

The present invention is a method to determine the TAN and TAN as a function of boiling point for a hydrocarbon feedstream using an electrospray ionization mass spectrometer (ESI-MS). The steps of the method include determining the signal as a function of mass from the ESI-MS while minimizing the formation of oligomers and fragmentation of the molecular species in the feedstream and then determining the TAN from the signals. The TAN is also determined as a function of boiling point.

14 Claims, 14 Drawing Sheets

TAN numbers determined by ESI-MS and by titration

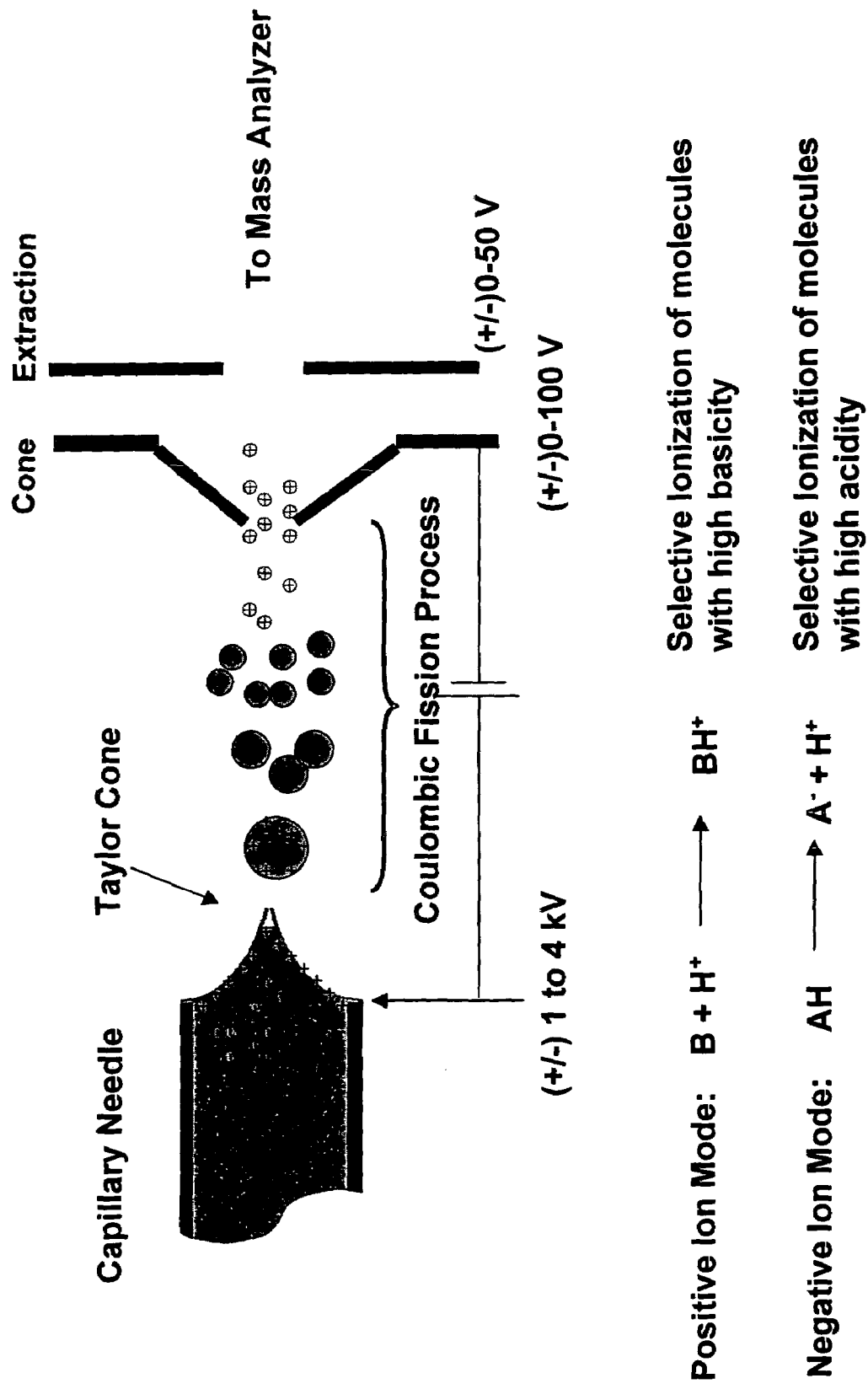
Figure 1. Electrospray Ionization Mechanisms

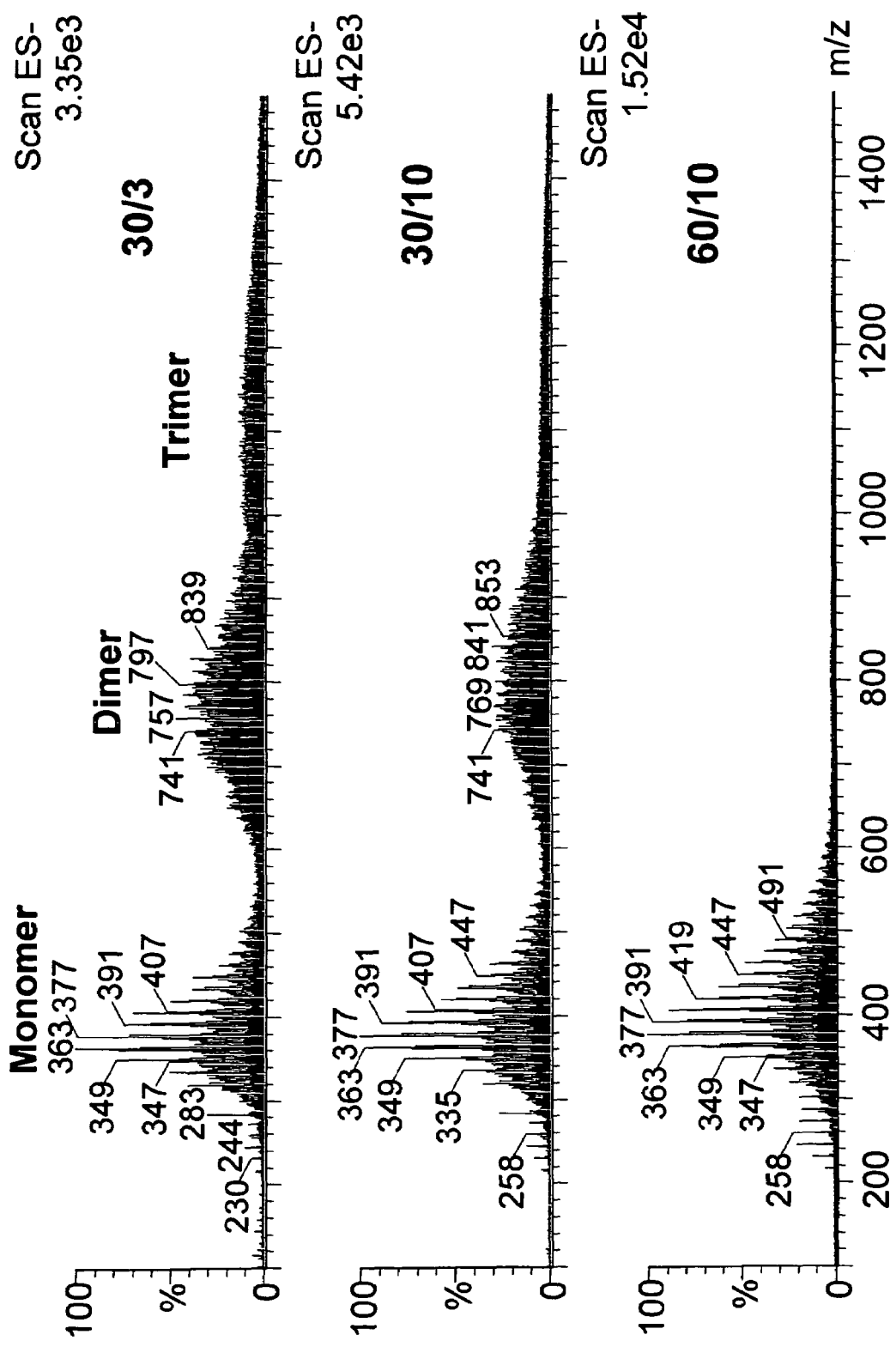
Figure 2. Low Cone/Extraction Voltages Promote Oligomer Formation (Negative Ion ESI)

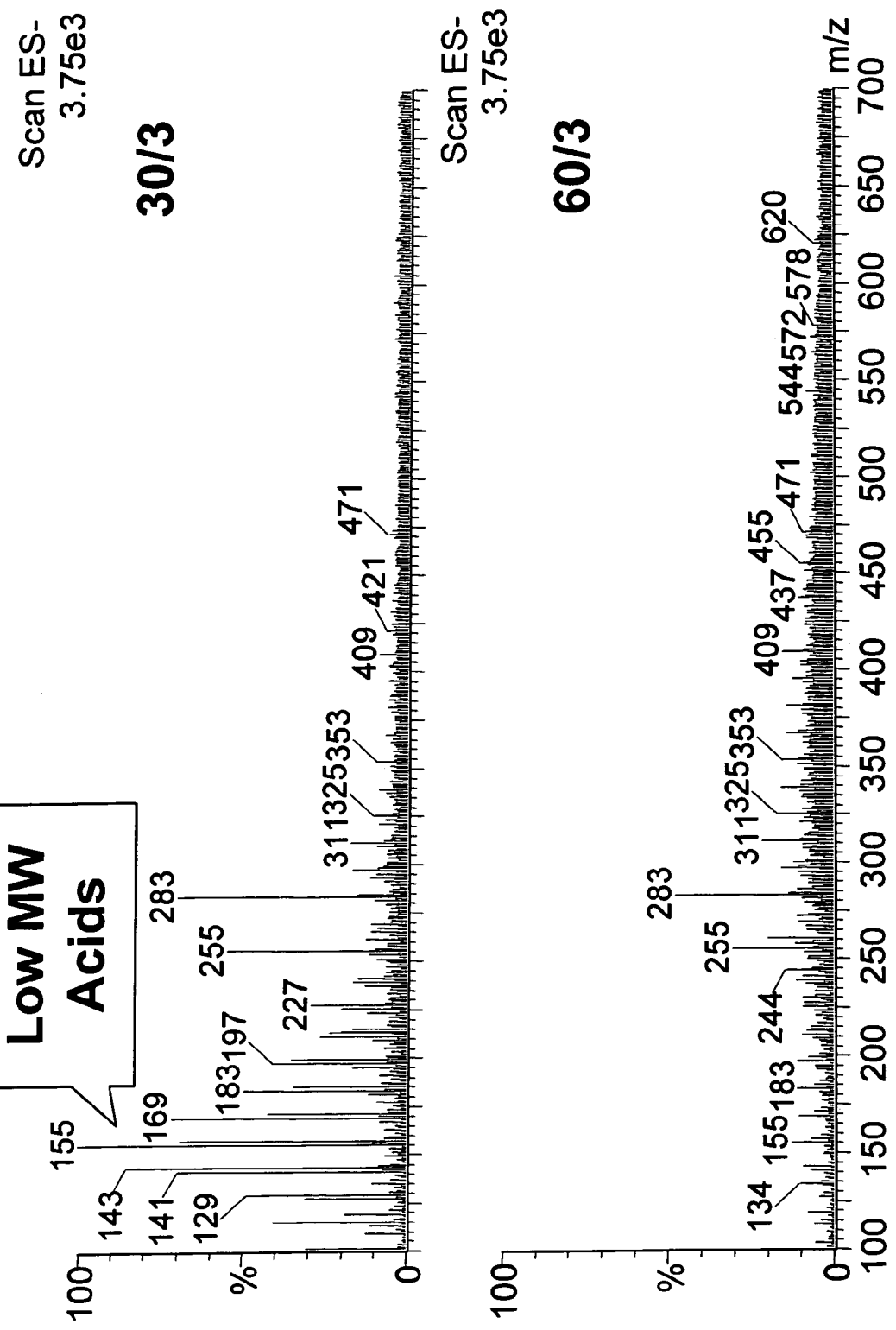
Figure 3. High cone/extraction voltage induce fragmentation of low molecular weight acids

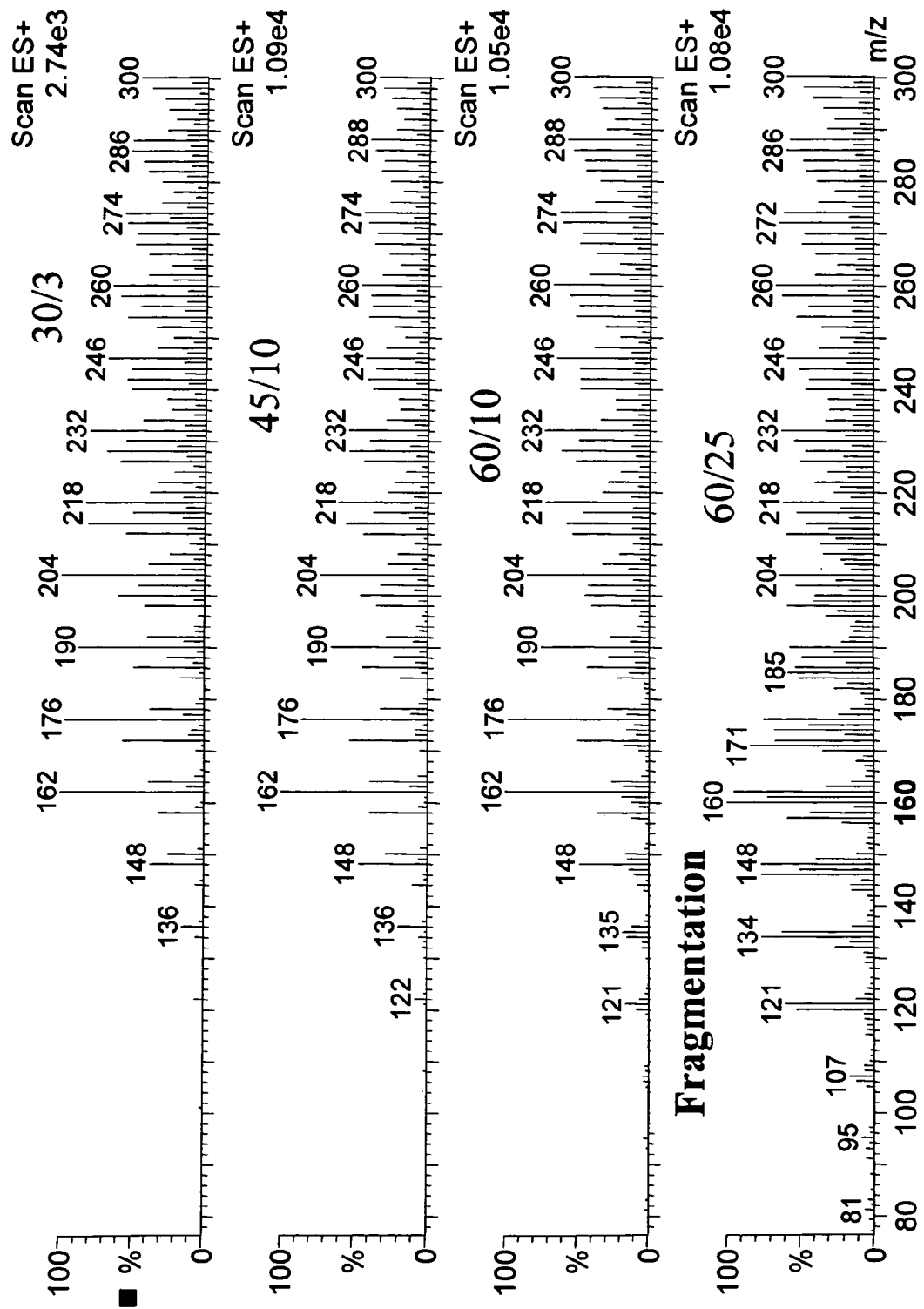
Figure 4. High cone/extraction voltage induce fragmentation of low molecular weight bases

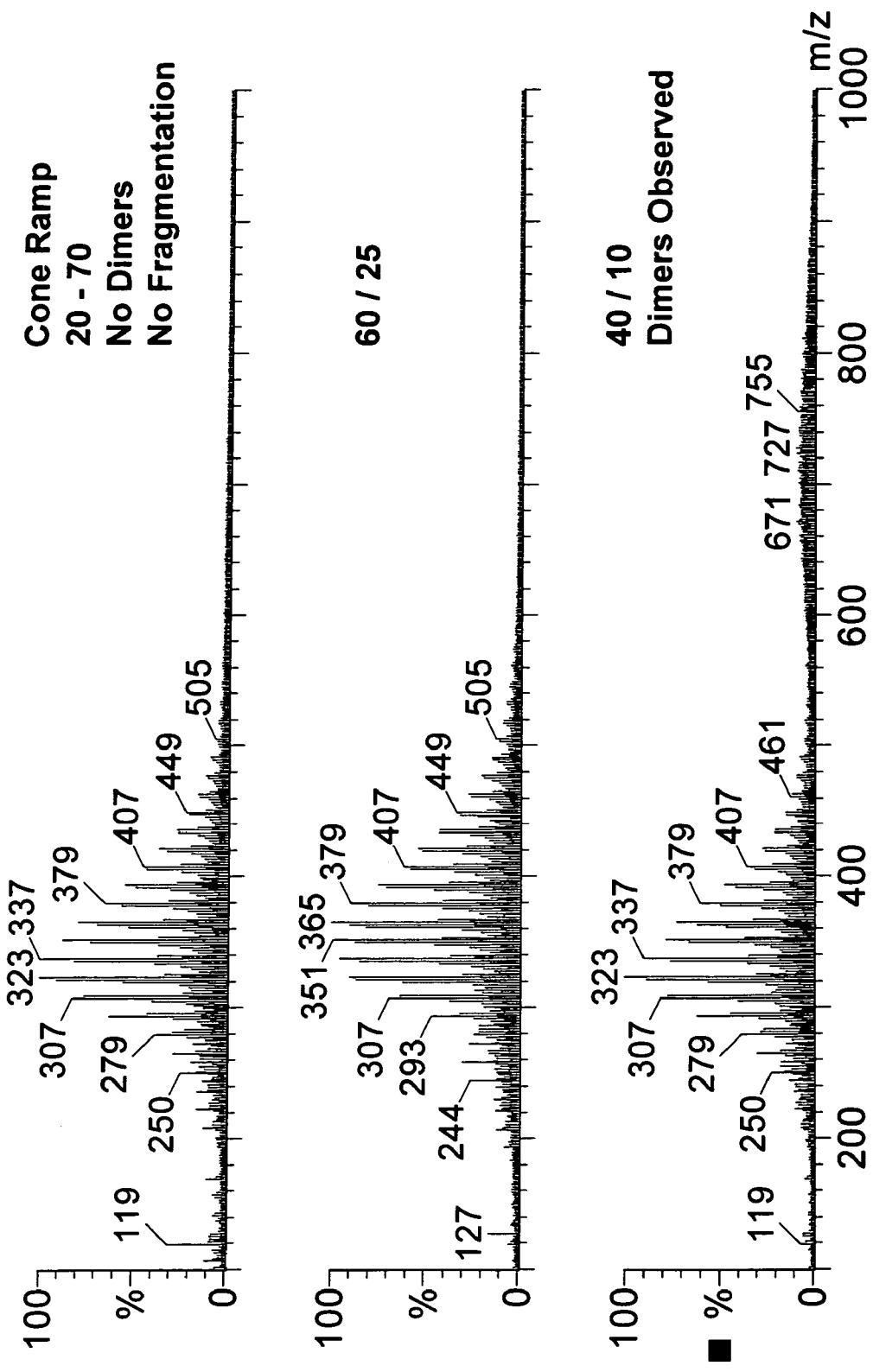
Figure 5. Ramping cone voltage minimizes dimers

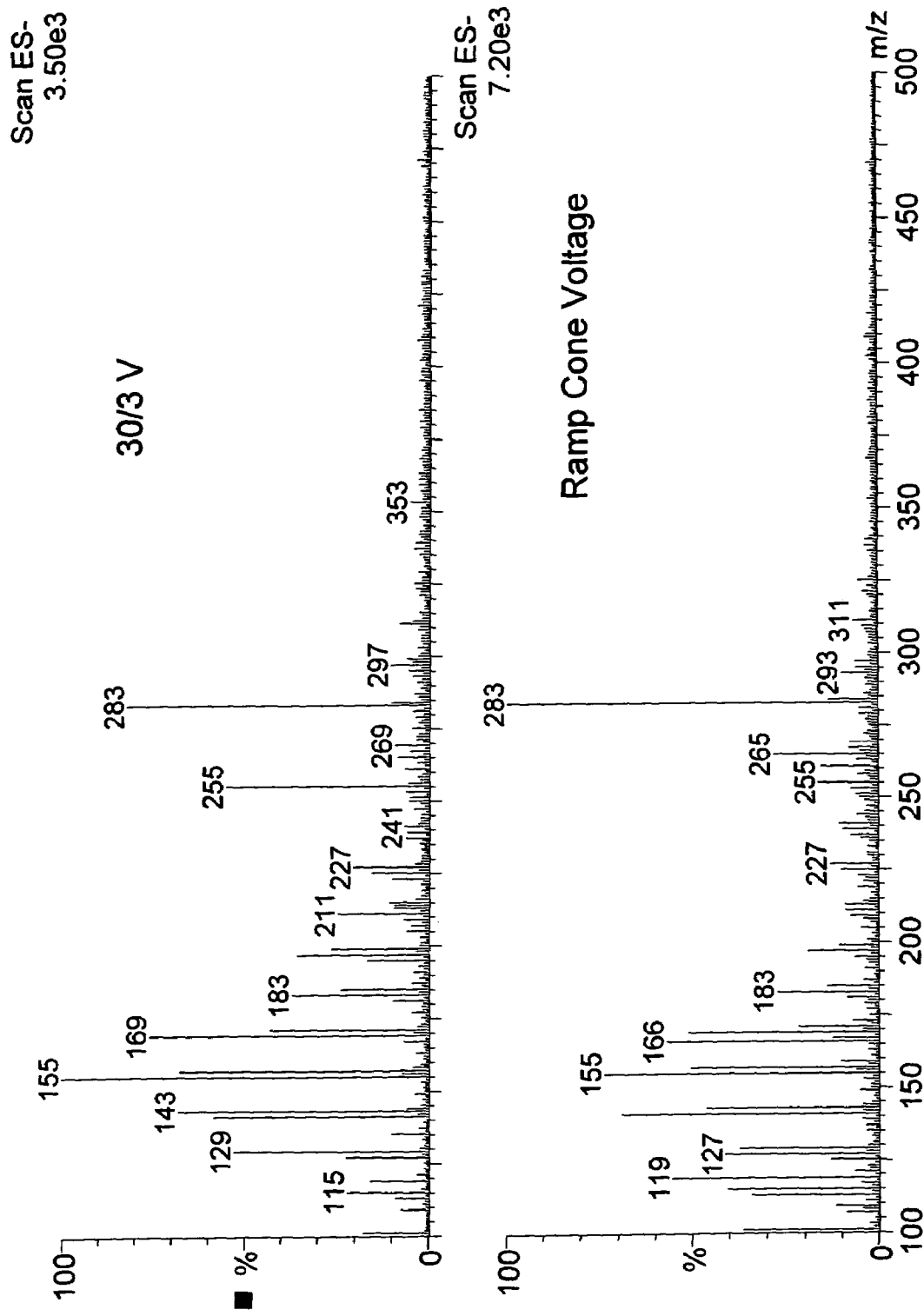
Figure 6. Ramping cone voltages minimizes fragmentation

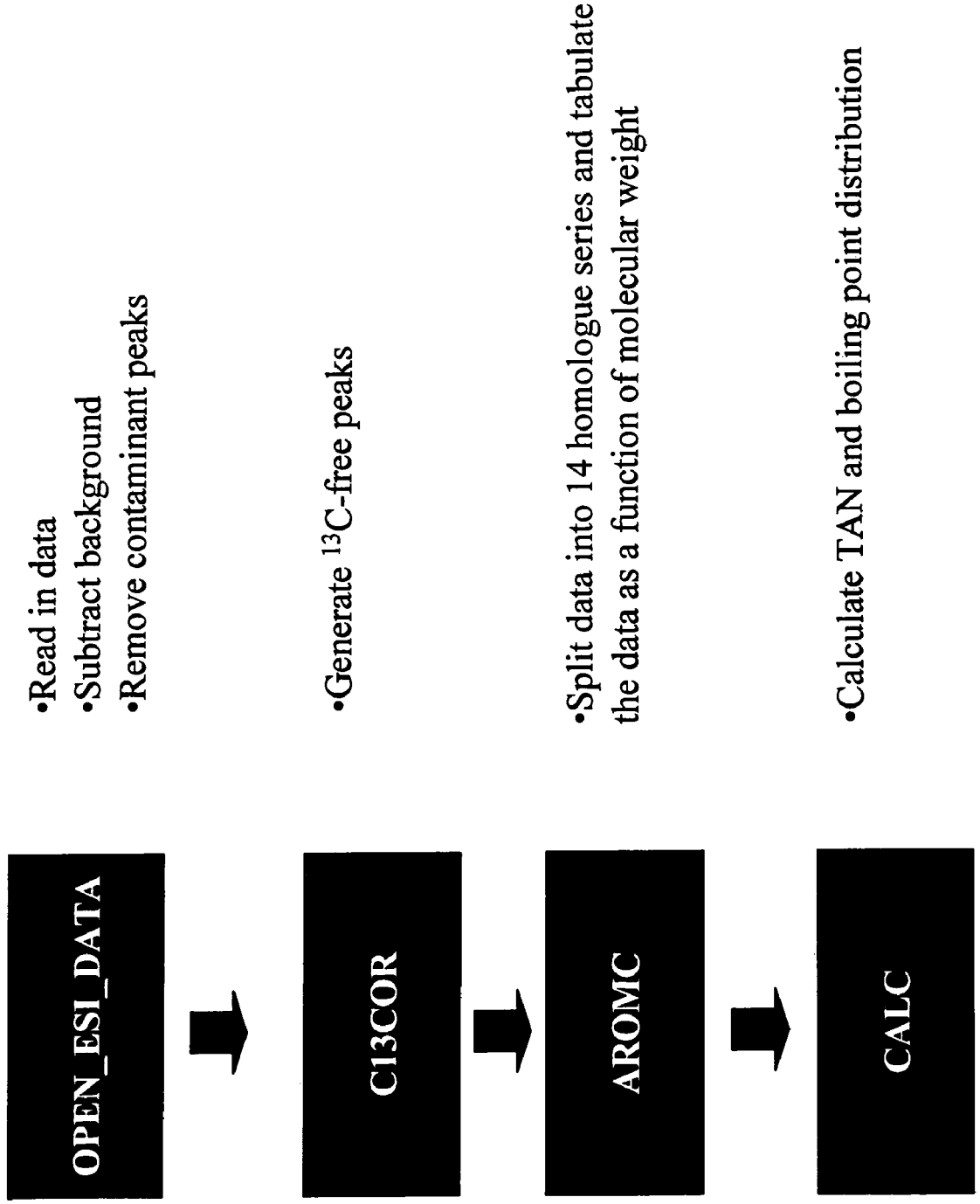
Figure 7. Flow diagram of data analysis

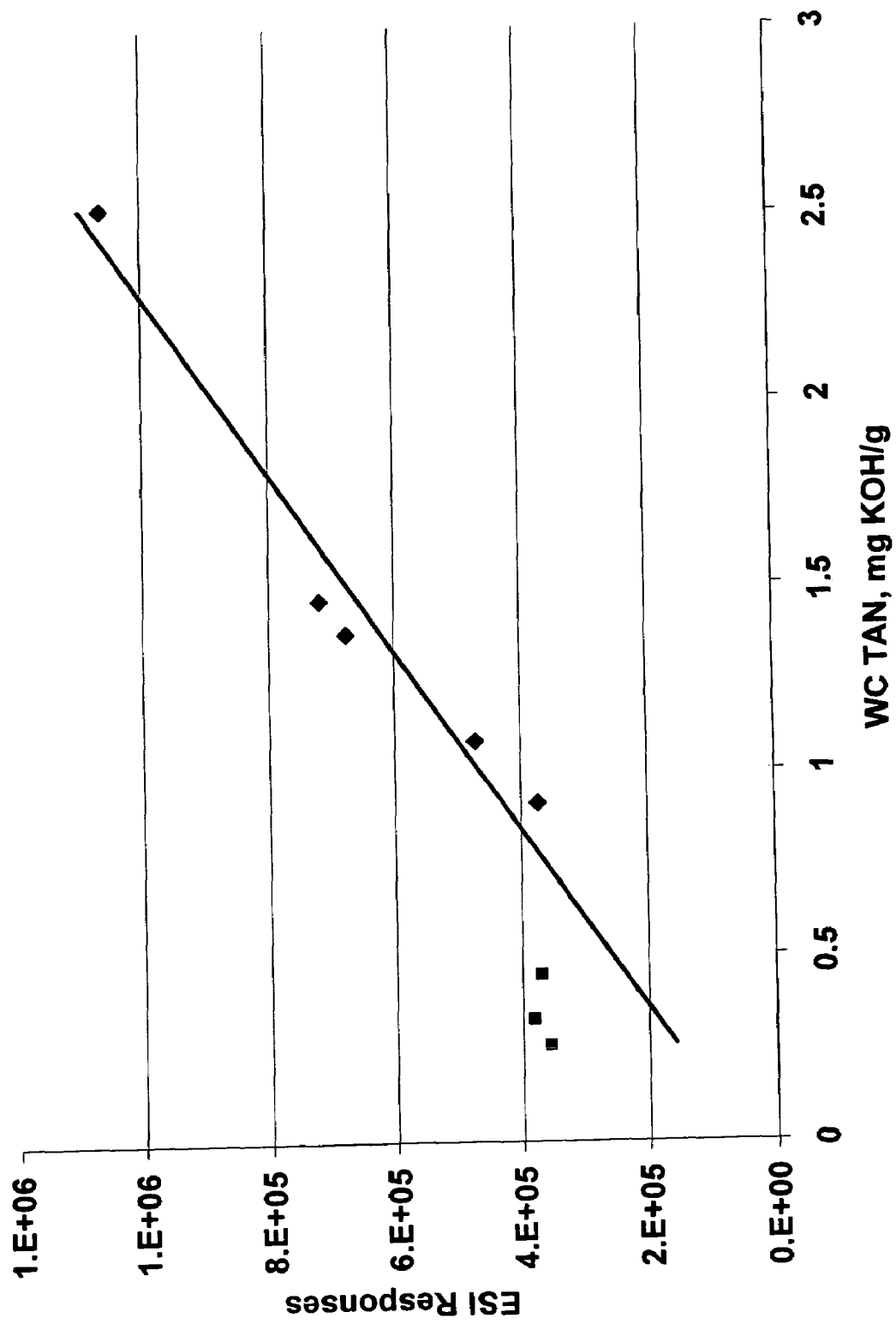

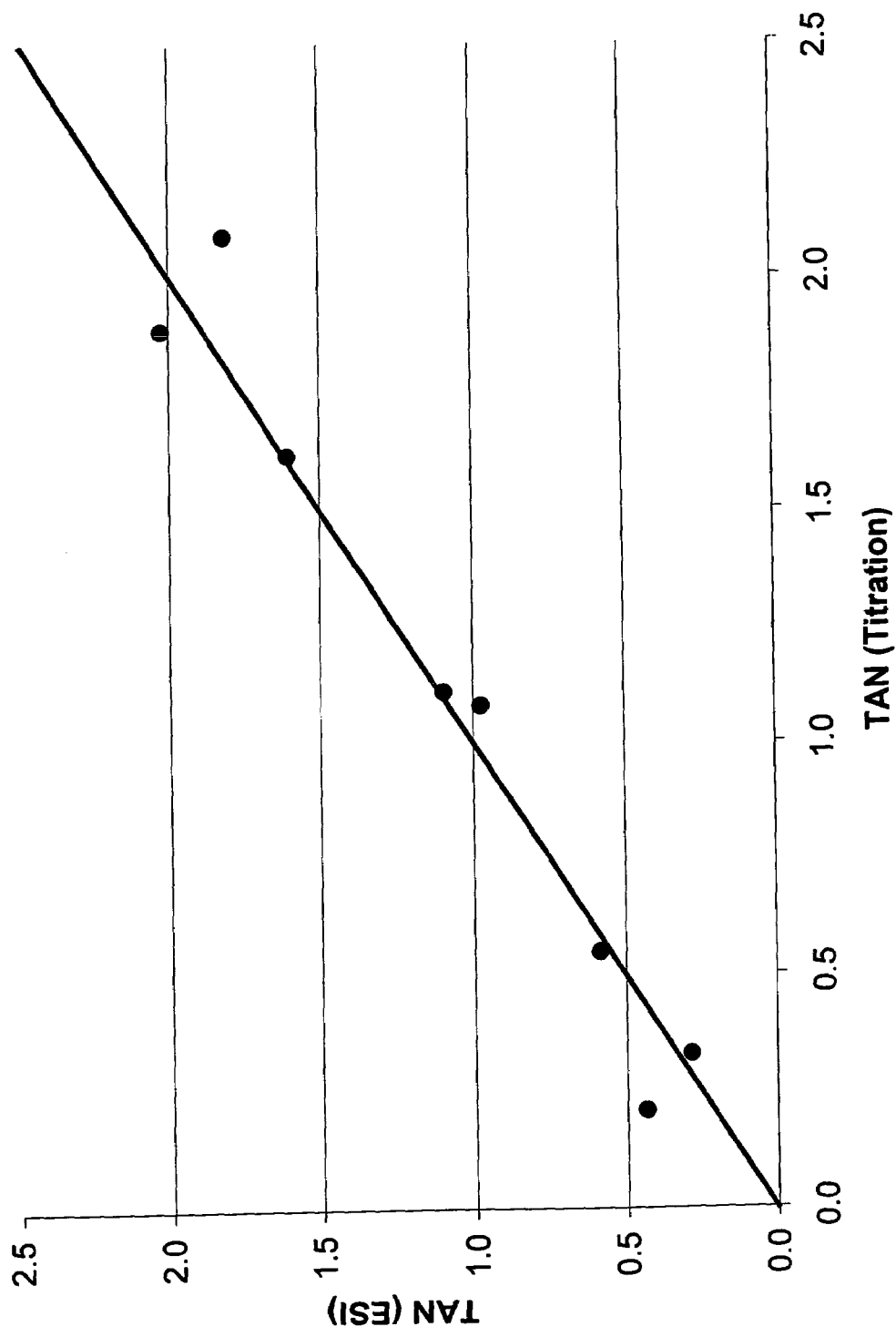
Figure 9. TAN numbers determined by ESI-MS and by titration

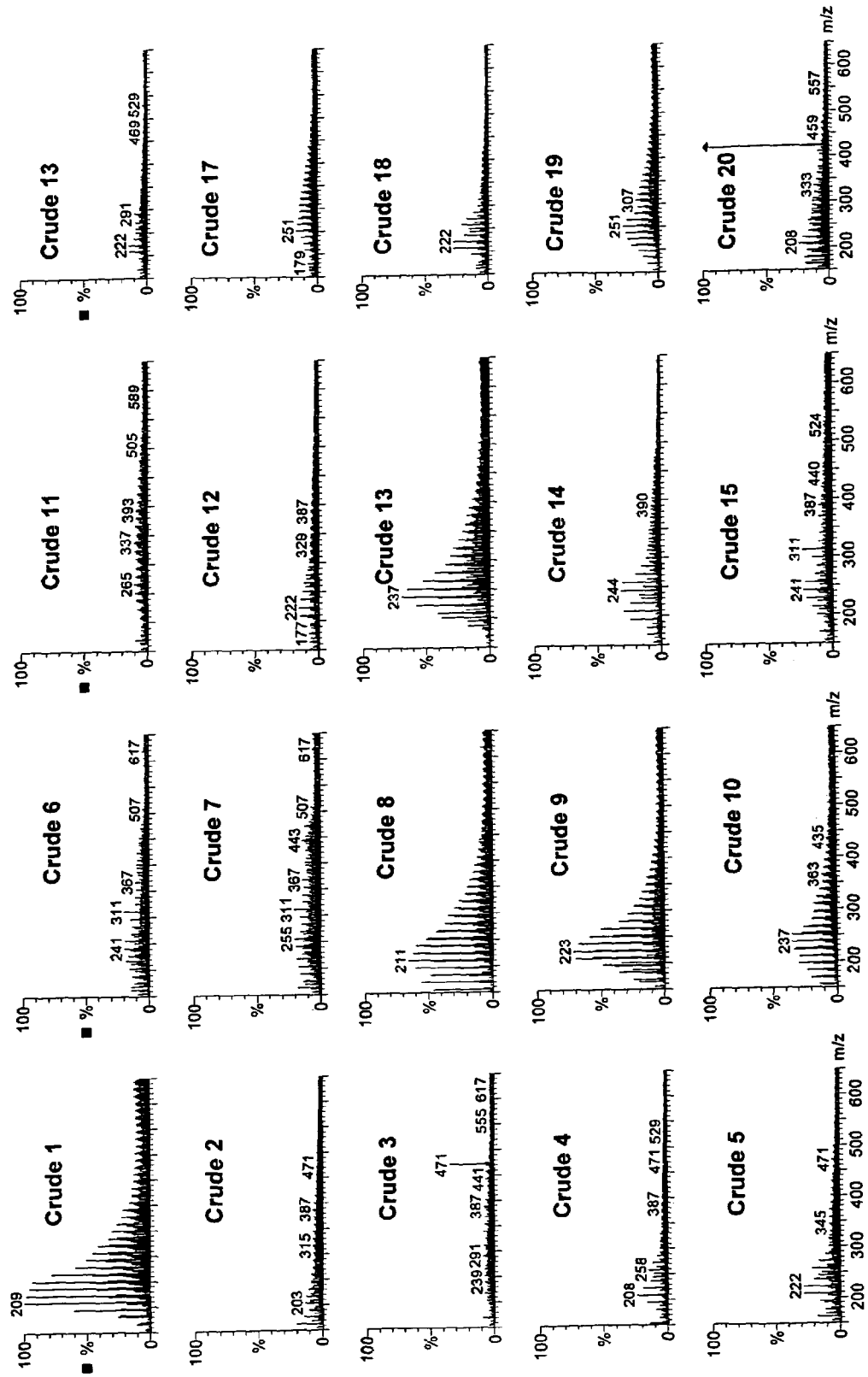
Figure 10. Negative ion ESI-MS spectra of 20 crude oils

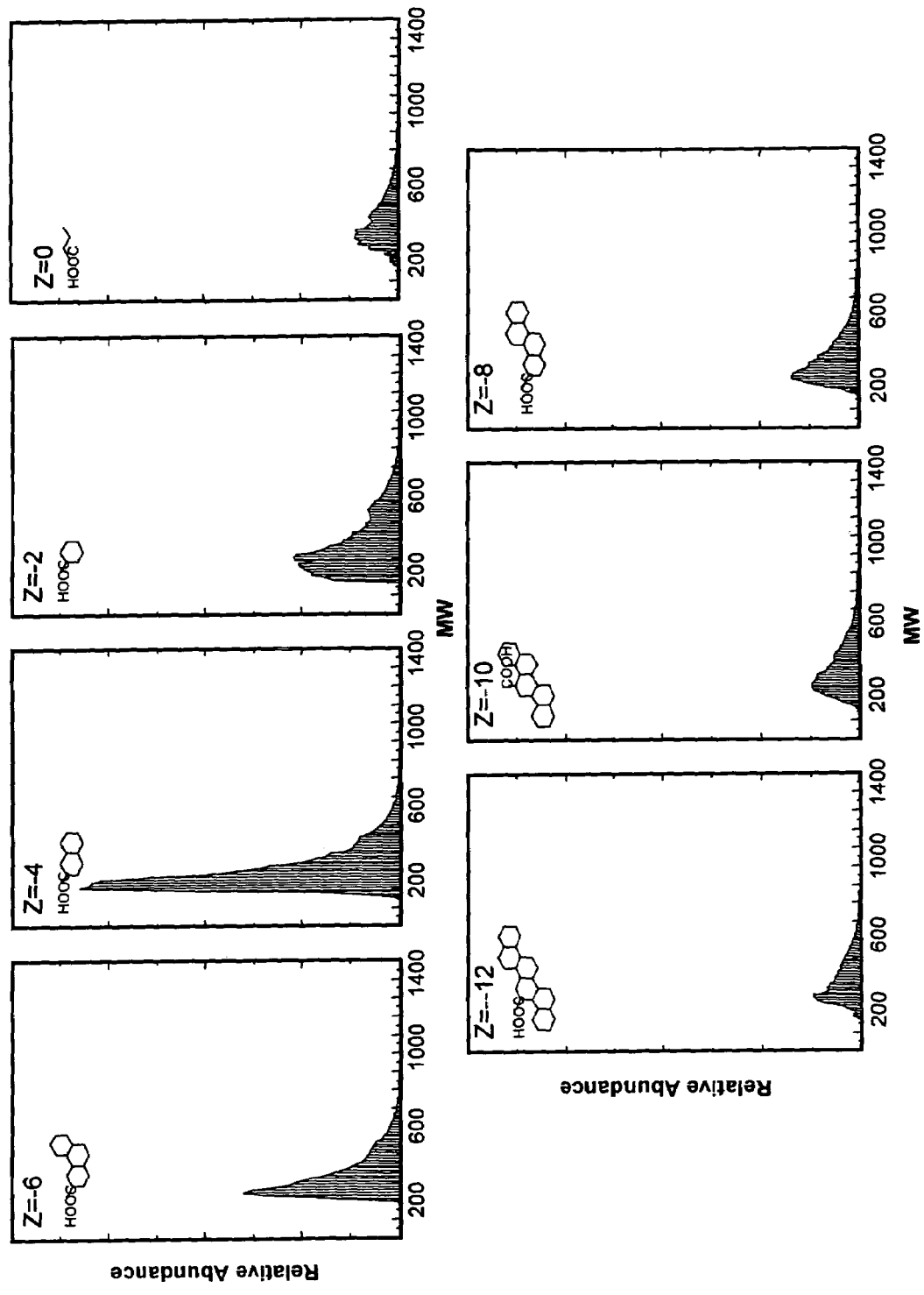

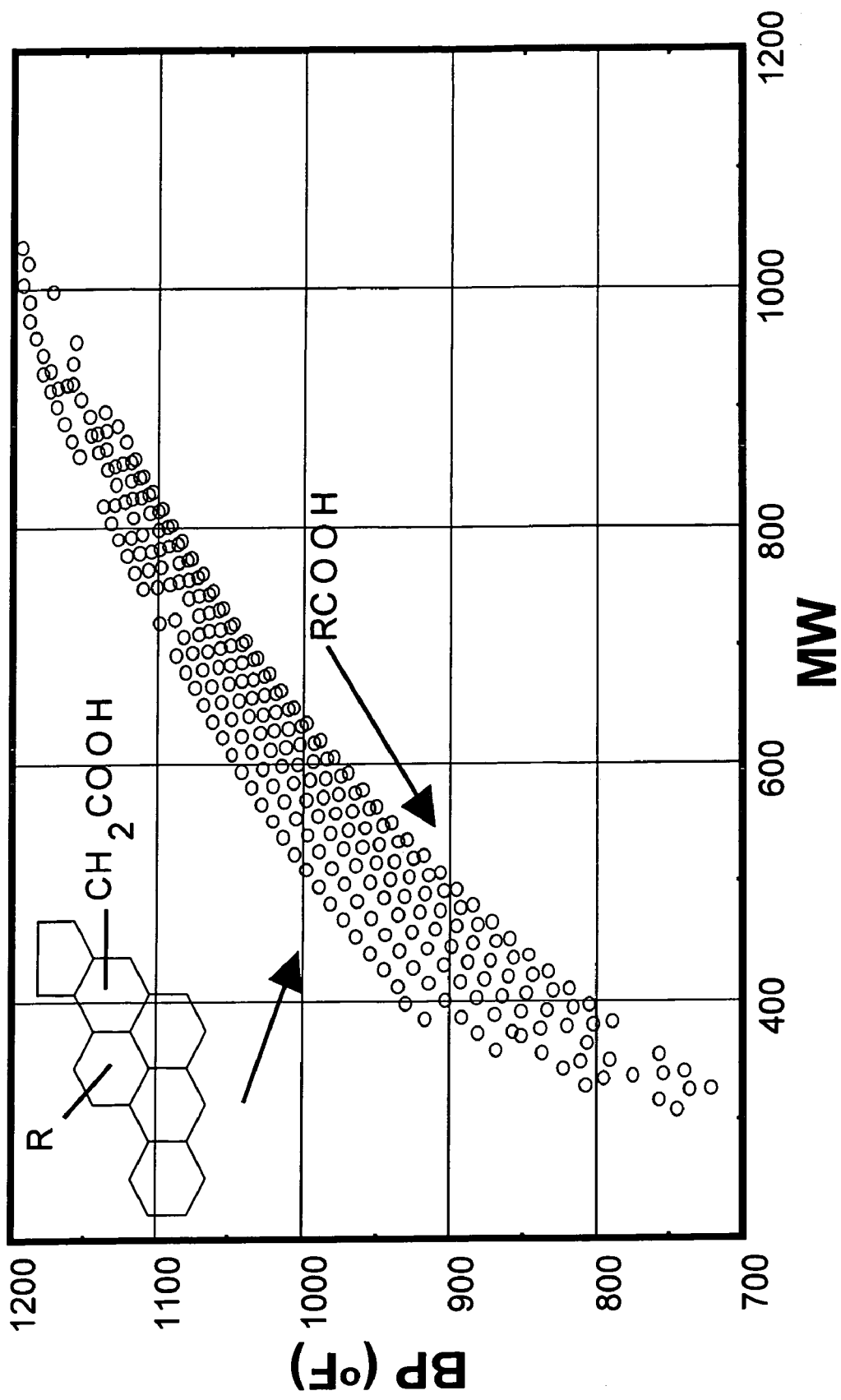
Figure 12. Boiling point - structure correlations of 7 acid types

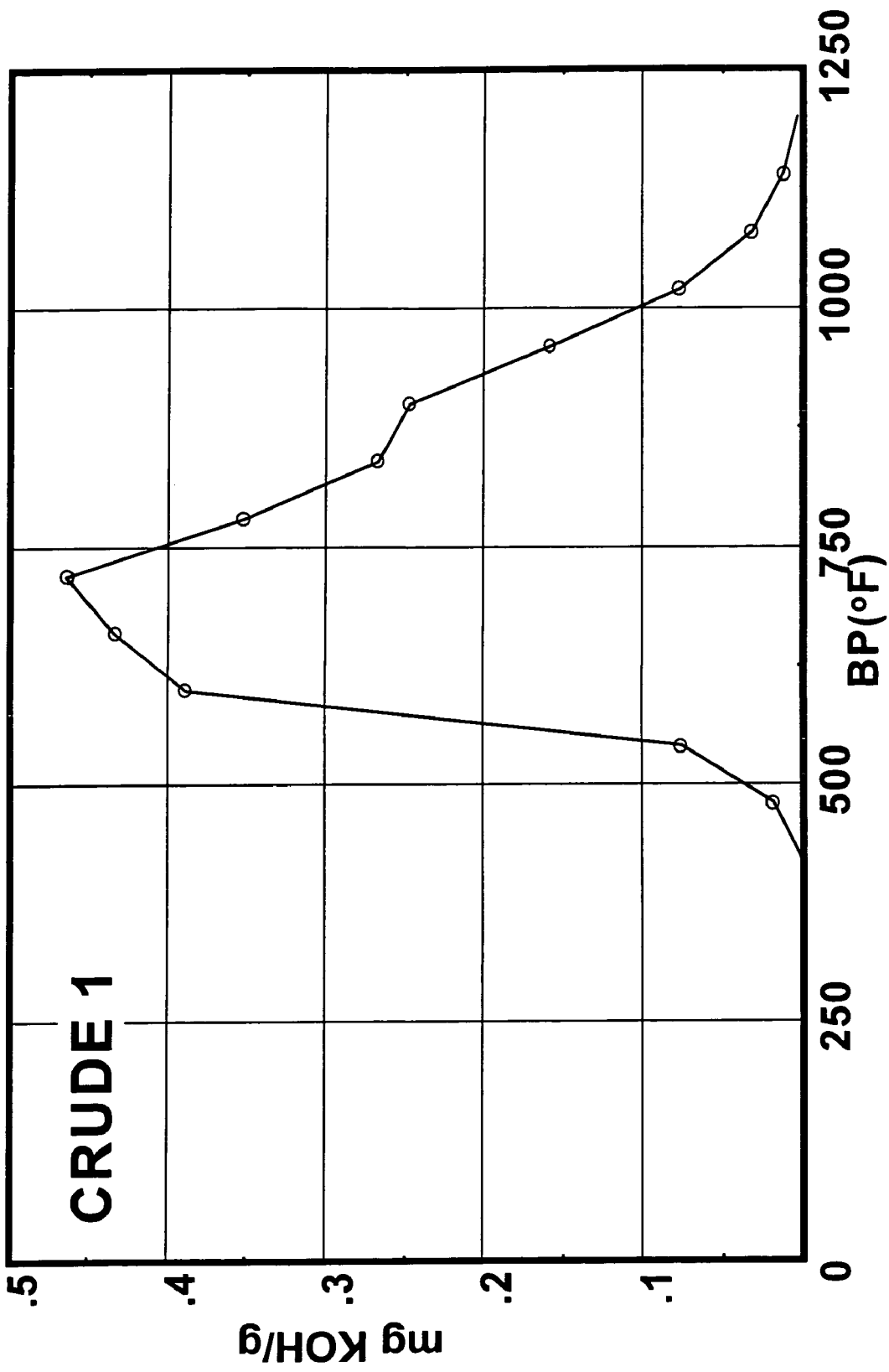
Figure 13. TAN distribution of crude 1

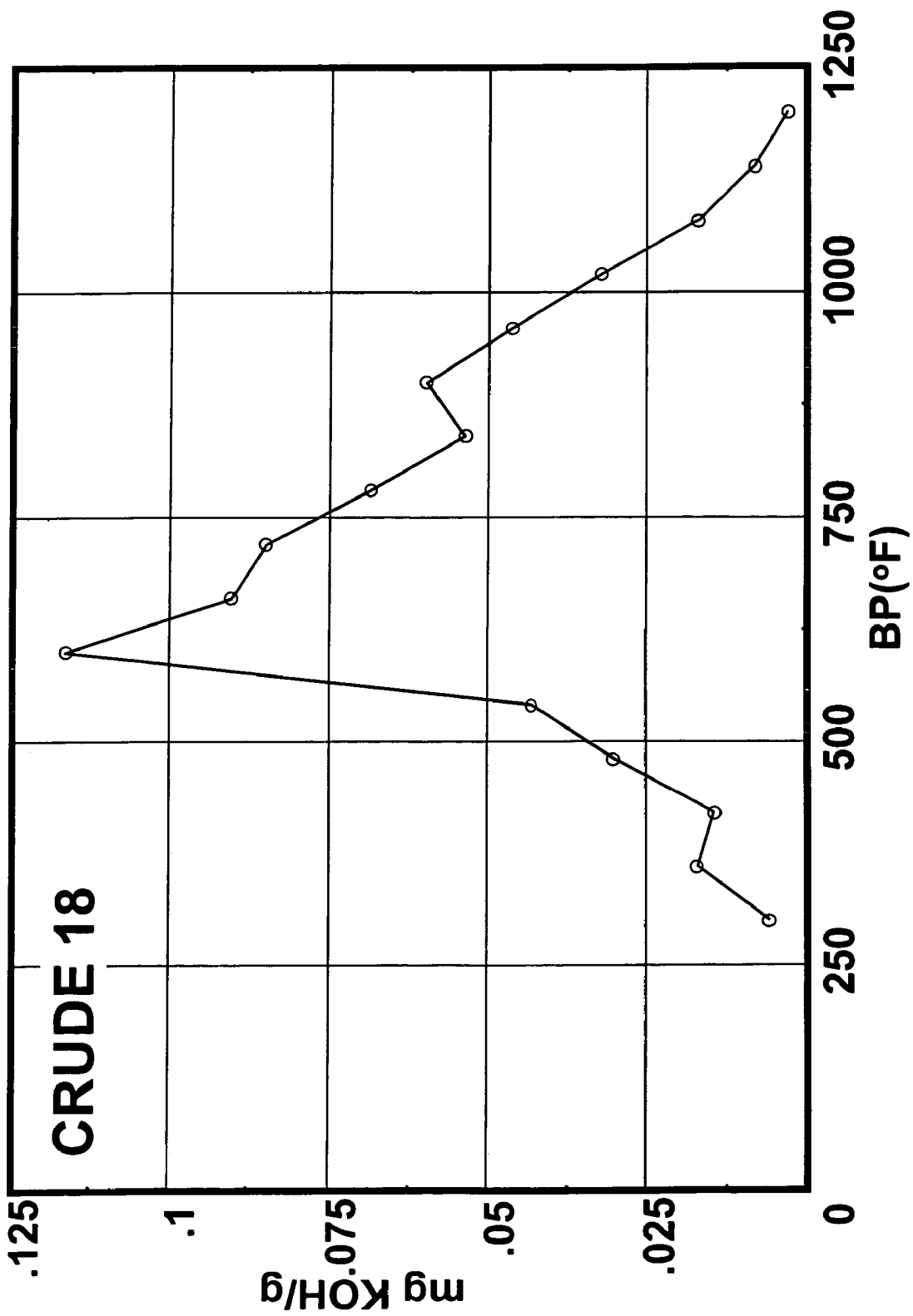
Figure 14. TAN distribution of crude 18

MEASUREMENT OF DISTRIBUTED TOTAL ACID NUMBERS BY ELECTROSPRAY MASS SPECTROMETRY

This application claims the benefit of U.S. Provisional application 60/707,706 filed Aug. 12, 2005.

The present invention relates to a method of determining the total acid number (TAN) of a hydrocarbon feedstream. In particular, the invention is a method for determining the TAN as a function of boiling point for a hydrocarbon feedstream to a refinery.

Total acid number (TAN) and TAN as a function of boiling point (distribution of TAN) are important assay properties that impact refinery optimization, corrosion management and safe refining of high TAN crudes. TAN is traditionally determined by non-aqueous titration. Distribution of TAN is determined by the measurement of TAN on selected distillation cuts. Extrapolation is typically performed to define the entire TAN distribution. It has been widely recognized and documented that TAN distribution at the high boiling range can be severely distorted due to the thermal decomposition of naphthenic acids.

In recent years, Electrospray ionization mass spectrometry (ESI-MS) has been rapidly explored to characterize polar compounds in petroleum systems. It has been demonstrated that acidic and basic compounds can be selectively ionized and detected by mass spectrometry. Accurate quantification of acid or base distributions, however, are difficult due to issues related to background carry-over, robustness in obtaining stable Electrospray of hydrocarbon samples, and a large number of factors influencing ESI responses of various compound classes and their mass distributions.

In the present invention, ESI-MS has been adopted to determine the TAN and TAN as function of boiling point for a hydrocarbon feedstream.

SUMMARY OF THE INVENTION

The present invention is a method to determine the TAN and the TAN as a function of boiling point for a hydrocarbon feedstream using an electrospray ionization mass spectrometer (ESI-MS). The steps of the method include determining the signal as a function of mass from the ESI-MS while minimizing the formation of oligomers and fragmentation of the molecular species in the feedstream and then determining the TAN from the signals. In a preferred embodiment, the TAN is determined as a function of boiling point. This is achieved by determining the signals of the ESI-MS for each mass and acid structure and combining signals of the ESI-MS having about the same known boiling point.

BRIEF DESCRIPTION OF THE DRAWINGS

FIG. 1 shows a schematic of an Electrospray Ionization Mechanism.

FIG. 2 shows that Low Cone/Extraction Voltages promote Oligomer Formation (Negative Ion ESI).

FIG. 3 shows that High Cone/Extraction Voltage induces fragmentation of Low Molecular Weight Acids.

FIG. 4 shows that High Cone/Extraction Voltage induces fragmentation of Low Molecular Weight Bases (Positive Ion ESI).

FIG. 5 shows that Ramping Cone Voltage minimizes Dimers (Negative Ion ESI).

FIG. 6 shows that Ramping Cone Voltages minimizes fragmentation (Negative Ion ESI).

FIG. 7 shows Flow Diagram of Data Analysis.

FIG. 8 shows ESI-MS Responses versus TAN numbers.

FIG. 9 shows TAN numbers determined by ESI and by Titration (Refinery Sidestreams).

FIG. 10 shows Negative Ion Esi-MS Spectra of 20 crude oils.

FIG. 11 shows the MW distribution of 7 acid types.

FIG. 12 shows the boiling point—structure correlations of 7 acid types.

FIG. 13 shows the TAN distribution of Crude 1.

FIG. 14 shows the TAN distribution of Crude 18.

DETAILED DESCRIPTION OF THE PREFERRED EMBODIMENTS

The present invention is a method that uses electrospray ionization mass spectrometry to directly measure total acid number and distributed total acid numbers (TAN) in petroleum products without distillating the sample. The method is based on selective ionization and detection of naphthenic acids in a hydrocarbon matrix by Electrospray Ionization Mass Spectrometry under negative ion conditions. The method determines composition of naphthenic acids including core structures and carbon number distributions. Boiling point distributions of TAN values are calculated based on the knowledges of structure boiling point correlations.

EXAMPLE

The stock solution of the negative ion standard was made by dissolving 38.3 mg of butyl hydroxy toluene, 39.4 mg of carbazole and 39.2 mg of stearic acid in 80 ml of toluene. The three compounds were used as internal standards for phenols, non-basic nitrogens and naphthenic acids, respectively.

About 200 mg of petroleum sample was dissolved in 3 ml of toluene and 17 ml MeOH. 0.1 ml $NH_4OH$ and 100 ul of the negative ion internal standard mentioned above were added to the solution. If particulates were formed, the solution was filtered with a 45 μm glass fiber filter before electrospray.

The mass spectrometry examples described in this invention were conducted on a Waters Quattro II Tandem Quadrupole Mass Spectrometry System. Electrospray experiments were conducted on an Advion NanoMate 100 that is based on 96 well sample introduction and a silicone chip containing 100 to 400 nozzles.

The conditions of ESI and mass spectrometry are as follows:

Nozzle voltage 1.5 to 1.75 kV
Delivering Pressure 0.15 to 0.20 psi
Mass Range: m/z 70 to 1000
Scan Speed: 3 sec/scan
Resolution: Unit Mass Resolution
Cone Voltage: ramped from 20 to 70 V as mass scanned from 70 to 1000 amu.
Extraction Voltage: 3 to 25 V An illustrative diagram of the ESI process is shown in FIG. 1. In ESI, a large potential of approximately 2,000 to 4,000 V is applied to a capillary needle through which a sample solution containing electrolyte (e.g. acetic acid for positive ion or $NH_4OH$ for negative ion) are introduced. A counter electrode is maintained at 0 V, thus creating a strong electric field between it and the capillary. The electric field permeates the solution at the capillary needle tip and causes separation of the ions in solution. In negative ion conditions, positive ions move toward the center of the capillary whereas negative ions are enriched at the surface of the liquid at the capillary tip. The repulsion of the excess charges at the surface and the pull of the electric field form a "Taylor cone" at the tip of capillary. As the charge repulsion overcome the surface tension of the liquid, a fine spray of charged droplets is created. As those droplets pass through a heated capillary within the mass spectrometer, the solvent evaporates, increasing the surface charge density. Coulombic repulsion causes droplets to fission into successively smaller daughter droplets, resulting in the eventual removal of all solvent molecules to yield unhydrated gas-phase ions (charge residual model) or direct ejection of ions into gas phase (ion evaporation model).

A chip-based nano electrospray (NanoMate 100) was introduced to improve the robustness and throughput of the ESI measurements. The system uses a conductive pipette tip to draw sample from a 96 well plate. The sample-filled tip aligns with a nozzle inlet on the back of the disposable ESI Chip, creating a tight seal. Each pipette tip and nozzle is used only once, providing a unique path into the mass spectrometer and eliminating sample carryover. The ESI Chip is analogous to the integrated circuit that enabled the mainframe-to-PC shift. It contains an array of nanoelectrospray nozzles (10×10 in low density chip and 20×20 in high density chip), each one-fifth the diameter of a human hair, etched in a standard silicon wafer. The chip-based nano-electrospray system was manufactured by Advion BioSciences Inc. The system enabled high throughput measurement (20 samples/hour or 3 minutes/sample).

In ESI, non-covalent interactions between ions and neutrals in liquid phase can be preserved in gas phase and be detected by mass spectrometry. Consequently, dimers (sometimes even higher order oligomers) were observed in addition to the monomers.

The ESI ions and non-covalent ion complexes are present in the following forms:
Monomers: $(M_i-H)^-$,
Dimers: $(M_i.M_j-H)^-$,
Trimers $(M_i.M_j.M_k-H)^-$ ... etc.

where I, j, k ranges from 1 to n and n is the total number of monomers. In our applications, the formation of higher order oligomers are not desired as they alter the MW distributions of analytes and consequently distort the boiling point distributions of the species.

The degree of non-covalent interaction can be controlled by a combination of cone and extraction voltages used to guide the ions from ESI tip into the mass spectrometer. The effect is illustrated by FIG. 2, which shows both dimers and trimers existing at 30/3 V (Cone/Extraction voltages) conditions. Trimers were eliminated by raising the extraction voltage to 10 V. Both dimers and trimers were eliminated when cone and extraction voltages were increased to 60 V and 10 V, respectively. The reduction of oligomer peaks at higher cone and extraction voltages is due to the collision-induced dissociation effect in the ionization region. Ions are subjected to a series of collisions with gas molecules prior to entering to the mass spectrometer. The effective collision energy is determined by both cone and extraction voltages.

$$E_{eff} = aV_{cone} + bV_{ext} \qquad \text{Equation 1}$$

Although high cone and extraction voltages can reduce the formation of high order oligomers, they have adverse effects on the ionization of low molecular weight species. In specific, it induces fragmentation in both negative ion and positive conditions as illustrated in FIG. 3 and FIG. 4, respectively. It is difficult to compromise the needs of dissociating oligomers while maintaining minimal fragmentation with constant cone and extraction voltages.

By examining samples of different molecular weight distributions, we discovered that higher molecular weight species are more difficult to fragment than the low molecular weight species. This is due to energy partition per molecule bond is less for the larger molecules than for the smaller molecules. We also noted that the molecular weights of the dimers are typically beyond 300 Da. Thus by ramping cone voltage against mass would both minimize the fragmentation of low molecular weight species while fragmenting non-covalent ion complexes at the high molecular weight region.

This hypothesis was confirmed when the cone voltage was ramped from 20 to 70 V while mass is scanned from 100 to 1000. The effective cone voltages at various masses are shown in Table 1. FIG. 5 showed that dimer formation is depressed by the ramped cone voltage conditions and FIG. 6 showed that low MW acids remain intact under the same conditions. It confirm that dimers are effectively dissociated with no fragmentation of low molecular weight species.

TABLE 1

EFFECTIVE CONE VOLTAGES AT DIFFERENT MASSES

| Mass (m/z) | Effective Cone Voltage (V) |
|---|---|
| 100 | 20.0 |
| 110 | 20.6 |
| 120 | 21.1 |
| 130 | 21.7 |
| 140 | 22.2 |
| 150 | 22.8 |
| 160 | 23.3 |
| 180 | 24.5 |
| 200 | 25.6 |
| 250 | 28.3 |
| 300 | 31.1 |
| 350 | 33.9 |
| 400 | 36.7 |
| 450 | 39.5 |
| 500 | 42.2 |
| 550 | 45.0 |
| 600 | 47.8 |
| 650 | 50.6 |
| 700 | 53.4 |
| 750 | 56.1 |
| 800 | 58.9 |
| 850 | 61.7 |
| 900 | 64.5 |
| 950 | 67.3 |
| 1000 | 70.0 |

A flow diagram of the data analysis is shown in FIG. 7. The raw data was imported, background subtracted and converted into a Mass-Intensity matrix. $^{13}$C-isotope corrections were performed to generate isotope-free data. The nominal mass peaks were grouped into 14 homologue series, 7 even mass and 7 odd mass homologues, respectively. According to the nitrogen rules, acids and phenols have even masses. Their $^{13}$C isotopes and nitrogen-containing compounds have odd masses.

Acids can be described by a general chemical formula $C_nH_{2n+z}O_2$, where Z is the hydrogen deficiency which is determined by the number of double bonds and rings in the molecules $Z=-2(R+DB-1)$. The seven even mass series generated by ESI were grouped by their Z numbers, $Z=0, -2, -4, -6, -8, -10$ and $Z=-12$. The nominal mass series contains one or two structures based on the minimum carbon numbers of the core structures. Low-resolution mass spectrometry cannot resolve nominal mass overlaps. We assumed that naphthenic acids are the primary structures although aromatic acids containing 1 to 3 rings have been reported.

Table 2 lists nominal mass groups and corresponding acid structures. Phenol structures were added to account for the low molecular weight species.

TABLE 2

ASSIGNMENT OF ACID STRUCTURES

| | Z-Values | | | | | | |
|---|---|---|---|---|---|---|---|
| C# | 0 | −2 | −4 | −6 | | −8 | |
| 3 | 74 | | | | | | |
| 4 | 88 | | | | | | |
| 5 | 102 | | | | | 3 | 94 |
| 6 | 116 | 114 | | | | 3 | 108 |
| 7 | 130 | 128 | | | | 2 | 122 |
| 8 | 144 | 142 | | | | 2 | 136 |
| 9 | 158 | 156 | | | | 2 | 150 |
| 10 | 172 | 170 | 168 | | | 2 | 164 |
| 11 | 186 | 184 | 182 | | | 2 | 178 |
| 12 | 200 | 198 | 196 | | | 2 | 192 |
| 13 | 214 | 212 | 210 | | | 2 | 206 |
| 14 | 228 | 226 | 224 | 222 | | 2 | 220 |
| 15 | 242 | 240 | 238 | 236 | | 2 | 234 |
| 16 | 256 | 254 | 252 | 250 | | 2 | 248 |
| 17 | 270 | 268 | 266 | 264 | | | 262 |
| 18 | 284 | 282 | 280 | 278 | | | 276 |
| 19 | 298 | 296 | 294 | 292 | | | 290 |
| 20 | 312 | 310 | 308 | 306 | | | 304 |
| 21 | 326 | 324 | 322 | 320 | | | 318 |
| 22 | 340 | 338 | 336 | 334 | | | 332 |
| 23 | 354 | 352 | 350 | 348 | | | 346 |
| 24 | 368 | 366 | 364 | 362 | | | 360 |
| 25 | 382 | 380 | 378 | 376 | | | 374 |
| ... | ... | ... | ... | ... | | | ... |

1.

2.

3.

| | Z-Values | | | |
|---|---|---|---|---|
| C# | −10 | | −12 | |
| 3 | | | | |
| 4 | | | | |
| 5 | | | | |
| 6 | | | | |
| 7 | | | | |
| 8 | 3 | 134 | | |
| 9 | 3 | 148 | | |
| 10 | 3 | 162 | | |
| 11 | 2 | 176 | | |
| 12 | 2 | 190 | 3 | 188 |
| 13 | 2 | 204 | 3 | 202 |
| 14 | 2 | 218 | 3 | 216 |
| 15 | 2 | 232 | 2 | 230 |
| 16 | 2 | 246 | 2 | 244 |
| 17 | 2 | 260 | 2 | 258 |
| 18 | 2 | 274 | 2 | 272 |
| 19 | 2 | 288 | 2 | 286 |
| 20 | | 302 | 2 | 300 |
| 21 | | 316 | 2 | 314 |
| 22 | | 330 | 2 | 328 |
| 23 | | 344 | | 342 |

TABLE 2-continued

| | | |
|---|---|---|
| 24 | 358 | 356 |
| 25 | 372 | 370 |
| ... | ... | ... |

1. [structure with COOH] [structure with HOOC]

2. [HOOC structure] [COOH structure]

3. [OH structure] [OH structure]

(all structures are 1 except those labeled 2 and 3)

The fundamental basis of E-TAN measurement is that electrospray signal is directly proportional to the level of acids in the sample, which in turn relates to the KOH needed to neutralize the acid. FIG. 8 illustrates the correlation between the total ESI-MS response and TAN values determined by the titration method. A linear correlation exists for high TAN crude (TAN>0.9 mg KOH/g). For low TAN crudes, interference of other acidic species (such as non-basic nitrogens and phenols) in crude oils exists. The nitrogen interference can be overcome by resolving odd and even masses.

TAN measurement by ESI is based on the quantification of all acid species in the sample by reference to an internal standard compound. In this work, stearic acid was used. We assumed uniform response factors for all acids molecules in the TAN calculation.

$$TAN(mg\ KOH/g) = (56.1/W) \times (M_S/R_S) \times \Sigma R_A \quad \text{Equation 2}$$

where W is the weight (g) of sample, $M_s$ is the mmole concentration of stearic acid, $R_S$ is the ESI response of the stearic acid and $R_A$ is the response of acid molecules in the sample.

FIG. 9 compares the TAN numbers determined by ESI with that by titration for a series of refinery side streams. The results agree well suggesting that the assumption of uniform response factor is reasonable.

One of the key advantages of Electrospray-TAN is that it can apply to whole crude and generate boiling point distributed TAN numbers without physically distilling the sample. FIG. 10 shows negative ion ESI-MS spectra of 20 crude oils. Both molecular weight distributions and intensities of ESI response vary with crude oils, suggesting that mass spectral fingerprints are correlated with the chemical compositions of the crude oil. In negative ion conditions, they are acidic compounds, including naphthenic acids, phenols and neutral or non-basic nitrogens such as carbazoles.

Once acid structures are specified as shown in FIG. 11, boiling points of all acid species can be calculated using structure-boiling point correlations well-known in the art. One example of such correlation is given in FIG. 12.

The assignments of boiling point properties to each of the molecules measured by E-TAN enabled "virtual cut" of specific boiling point fractions and calculation of TAN values for these fractions. Thus, the boiling point distribution of the TAN properties can be determined. FIG. 13 and FIG. 14 show TAN distributions of two crude oils by E-TAN. The trend in distributions agree well.

Therefore, the present invention shows that Electrospray Mass spectrometry can be used as a means for rapid and microscale measurement of TAN and TAN boiling point distributions for petroleum crude and products. The latter properties can be obtained without physically distilling the sample. Since ESI does not involve thermal processing, decomposition of naphthenic acids is minimized. The use of nano-electrospray technology greatly enhanced the repeatability and robustness of the method. A mass-dependent collision-induced dissociation was developed to eliminate dimers and minimize fragmentation of low MW acid. TAN values determined by the technique agree well with that by titration method.

What is claimed is:

1. A method to determine the Total Acid Number (TAN) distribution of a hydrocarbon feedstream comprising hydrocarbons and acidic compounds including naphthenic acids, the method comprising:
    (a) determining a mass spectrometry signal of said hydrocarbon feedstream as a function of mass of the ions from an electrospray ionization mass spectrometer (ESI-MS) operating under negative ion conditions, while ramping the effective collision energy of the ions as a function of the increase in mass of the detected species to minimize formation of oligomers and fragmentation;

(b) determining the TAN distribution of said hydrocarbon feedstream from said mass spectrometry signal.

2. The method of claim 1 wherein the effective collision energy of the electrospray ionization is ramped by increasing the cone voltage of said electrospray ionization mass spectrometer with increasing mass of the detected species.

3. The method of claim 2 wherein said cone voltage is ramped from 20 to 70v while mass is scanned from 100 to 1000 amu.

4. The method of claim 3 wherein said extraction voltage is increased from 3v to 10v as the cone voltage is ramped from 20 to 70v.

5. The method of claim 2 wherein the extraction voltage of said electrospray ionization mass spectrometer is increased as the cone voltage is ramped.

6. The method of claim 1 wherein the TAN of the sample is determined by summing of the mass spectrometry signals for all masses.

7. The method of claim 6 wherein said the masses corresponding to the mass spectrometry signals are determined by reference to an internal standard compound.

8. The method of claim 7 wherein said reference standard is stearic acid.

9. The method of claim 8 wherein said step of determining the TAN distribution as a function of boiling point includes determining the signals of the ESI-MS for each mass end acid structure.

10. The method of claim 7 wherein the TAN of the sample is determined by $$\text{TAN}(\text{mg}KOH/\text{g}) = 56.1(W) \times \left(\frac{M_S}{R_S}\right) \times \Sigma R_A$$

where W is weight(g) of sample $M_s$ is the mmole concentration of the reference standard, $R_s$ is the ESI response of the reference standard and $R_A$ is the response of acid molecules in the sample.

11. The method of claim 10 wherein said reference standard is stearic acid.

12. The method of claim 10 wherein said step of determining TAN as a function of boiling point includes combining signals of the ESI-MS having about the same known boiling point.

13. The method of claim 6 wherein said mass spectrometry signal from ESI-MS is directly proportional to said TAN.

14. The method of claim 1 further comprising the step of determining the TAN distribution as function of boiling point.

* * * * *